US010327935B2

(12) United States Patent
Davis et al.

(10) Patent No.: US 10,327,935 B2
(45) Date of Patent: Jun. 25, 2019

(54) STENT GRAFT WITH INTERNAL CONSTRAINING MECHANISM

(71) Applicant: COOK MEDICAL TECHNOLOGIES LLC, Bloomington, IN (US)

(72) Inventors: Brandon J. Davis, West Lafayette, IN (US); Jarin A. Kratzberg, Lafayette, IN (US); Blayne A. Roeder, Bloomington, IN (US); Edwin E. Macatangay, Bloomington, IN (US); Davorin K. Skender, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 106 days.

(21) Appl. No.: 15/216,023

(22) Filed: Jul. 21, 2016

(65) Prior Publication Data
US 2018/0021158 A1    Jan. 25, 2018

(51) Int. Cl.
*A61F 2/06* (2013.01)
*A61F 2/07* (2013.01)
*A61F 2/97* (2013.01)

(52) U.S. Cl.
CPC ............... *A61F 2/97* (2013.01); *A61F 2/07* (2013.01); *A61F 2002/061* (2013.01); *A61F 2002/067* (2013.01); *A61F 2002/075* (2013.01); *A61F 2250/0039* (2013.01)

(58) Field of Classification Search
CPC ........ A61F 2/07; A61F 2002/067; A61F 2/04; A61F 2/06; A61F 2002/072; A61F 2/97; A61F 2002/061; A61F 2002/075
See application file for complete search history.

(56) References Cited

U.S. PATENT DOCUMENTS

| 2001/0004707 | A1 | 6/2001 | Dereume et al. | |
|---|---|---|---|---|
| 2008/0147163 | A1* | 6/2008 | Allen | A61F 2/06 623/1.14 |
| 2011/0106115 | A1* | 5/2011 | Haselby | A61B 5/076 606/151 |
| 2013/0079870 | A1* | 3/2013 | Roeder | A61F 2/07 623/1.35 |
| 2013/0116775 | A1* | 5/2013 | Roeder | A61F 2/856 623/1.35 |

FOREIGN PATENT DOCUMENTS

EP    2749252 A1    7/2014

OTHER PUBLICATIONS

European Search Report for EP Application No. 17275113, dated Dec. 12, 2017, 6 pages.

* cited by examiner

*Primary Examiner* — Katrina M Stransky
(74) *Attorney, Agent, or Firm* — Brinks Gilson & Lione

(57) ABSTRACT

A stent graft assembly having a tubular body and a constraining patch attached to the interior surface of the tubular body. The constraining patch delineates a small passageway close to the inner surface of the tubular body. A cannula may extend through the passageway.

20 Claims, 6 Drawing Sheets

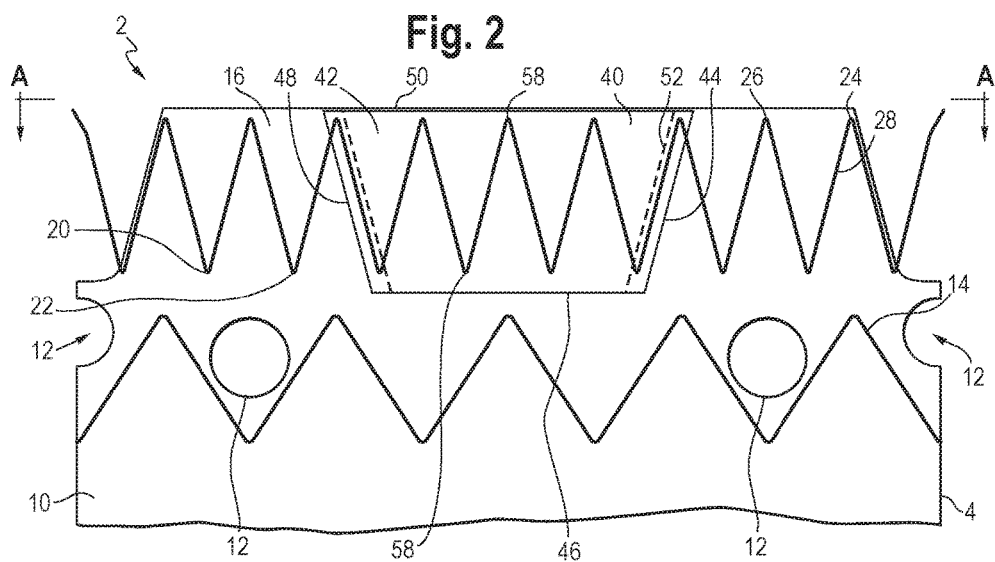
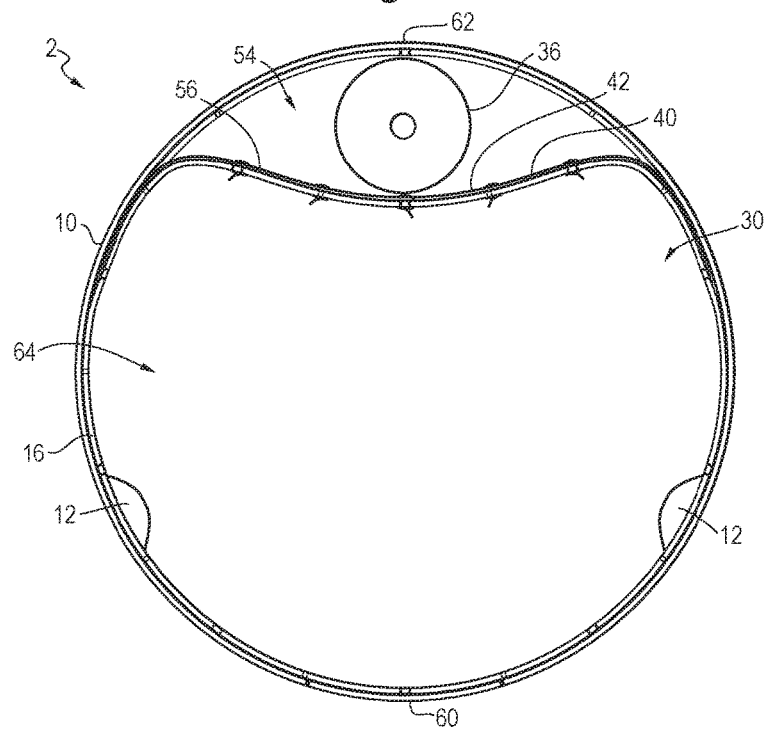

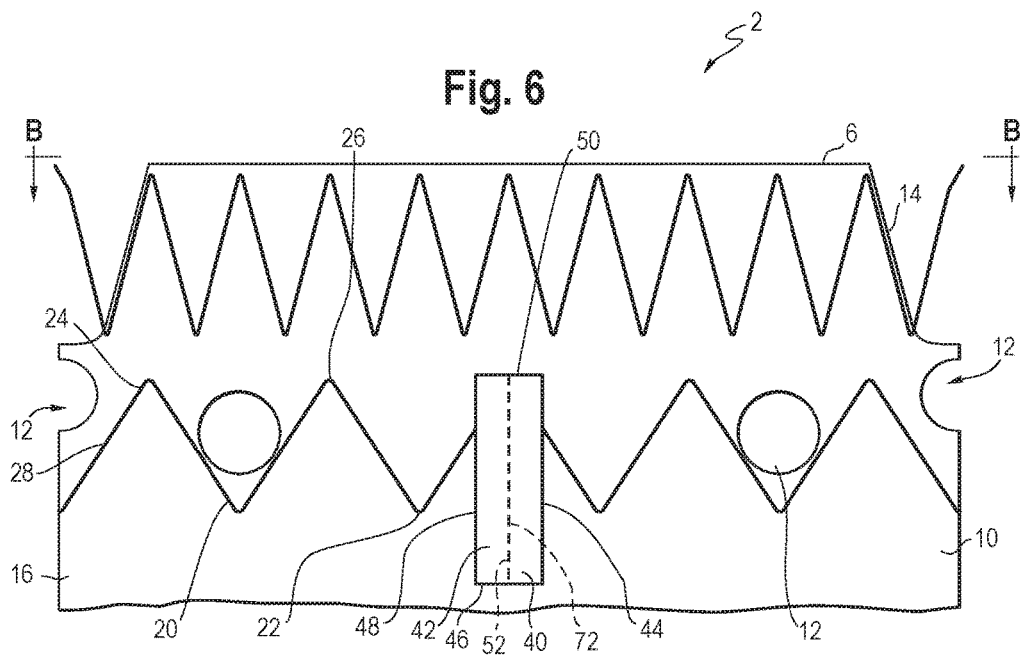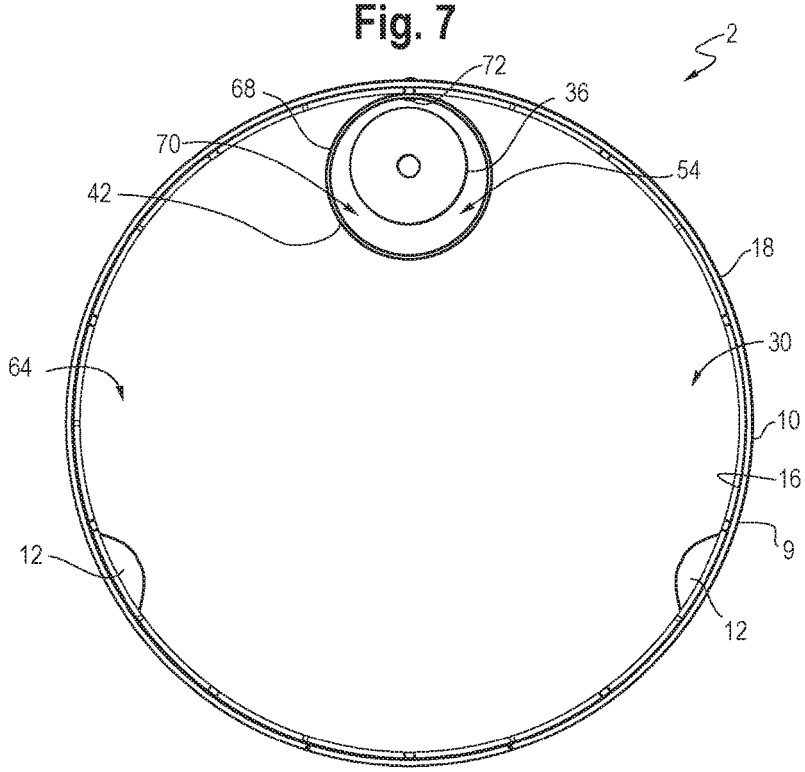

STENT GRAFT WITH INTERNAL CONSTRAINING MECHANISM

TECHNICAL FIELD

This disclosure relates generally to an endoluminal prosthesis and, in one example, to an intraluminal stent graft with an internal constraining patch. The constraining patch can control the path of a medical device travelling through a lumen in the prosthesis to avoid undesirable contact with other secondary structures in the lumen of the prosthesis.

BACKGROUND

Endoluminal prostheses may be inserted into a body lumen such as an anatomical vessel or duct for various purposes. Prostheses may maintain or restore patency in a formerly blocked or constricted passageway or they may be used for different procedures. For example, a prosthesis may include one or more stents disposed in or about a graft, and the stents may hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Modular stent graft pieces can be deployed in stages to form a combined stent graft assembly. First, a main or central stent graft piece can be deployed. Subsequently, secondary stent graft pieces can be deployed and positioned within the main stent graft piece. This type of staged deployment can require multiple cannulations of the main stent graft lumen.

When a secondary stent graft piece has been deployed and positioned within the main stent graft piece, further movement of a delivery or other device through the stent graft may result in unintended contact between the device and the deployed secondary pieces.

This disclosure describes an apparatus and methods designed to temporarily constrain such devices against a portion of an interior surface of a stent graft so as to avoid contact with secondary stent graft pieces.

SUMMARY

According to a first aspect of the present disclosure, there is provided a stent graft assembly comprising a tubular body having a first open end, a second open end, a main lumen between the first open end and the second open end, and an inner surface surrounding the main lumen; a patch disposed in the main lumen and attached to the inner surface and defining a longitudinally extending passageway between the inner surface and the patch, the patch having a first unattached end and a second unattached end; wherein the passageway is in fluid communication with the main lumen through the first unattached end and the second unattached end; wherein neither unattached end is in communication with an exterior of the graft, and wherein the patch is configured to temporarily constrain a portion of a medical instrument within the passageway.

According to a second aspect of the present disclosure, there is provided a stent graft assembly comprising a tubular body having a main lumen and an inner surface surrounding the main lumen; a patch disposed in the main lumen, the patch comprising a piece of material attached to the inner surface that forms a passageway that extends at least longitudinally along the patch and has a first open end and a second open end; wherein the passageway has a first configuration where a portion of the patch extends away from the inner surface and the passageway is open, and a second configuration where the patch lays flat against the inner surface and the passageway is closed.

According to a third aspect of the present disclosure, there is disclosed a stent graft assembly comprising: a tubular body having a main lumen and an inner surface surrounding the main lumen; a patch disposed in the main lumen and attached to the inner surface; the patch forming an constraining tube having a longitudinal constraining lumen extending therethrough, wherein the constraining tube has first and second open ends and wherein neither open end is exposed to an exterior of the tubular body.

BRIEF DESCRIPTIONS OF THE DRAWINGS

FIG. 2 shows a partial flattened view of the upper end of the internal surface of the stent graft assembly shown in FIG. 1.

FIG. 3 shows a latitudinal cross-sectional view of the stent graft assembly shown in FIG. 2 at line A.

FIG. 6 shows a partial flattened view of the upper end of the internal surface of the stent graft assembly shown in FIG. 4.

FIG. 7 shows a latitudinal cross-sectional view of the stent graft assembly shown in FIG. 6 at line B.

DETAILED DESCRIPTION

The present disclosure relates to apparatus and methods for delivering and deploying endoluminal prostheses in a body vessel, duct, or lumen. In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first), and the outflow end (that end from which the fluid exits).

FIGS. 1-8 show an endoluminal prosthesis. In a non-limiting example, the prosthesis shown in FIGS. 1-8 is a stent graft.

Figure 1:
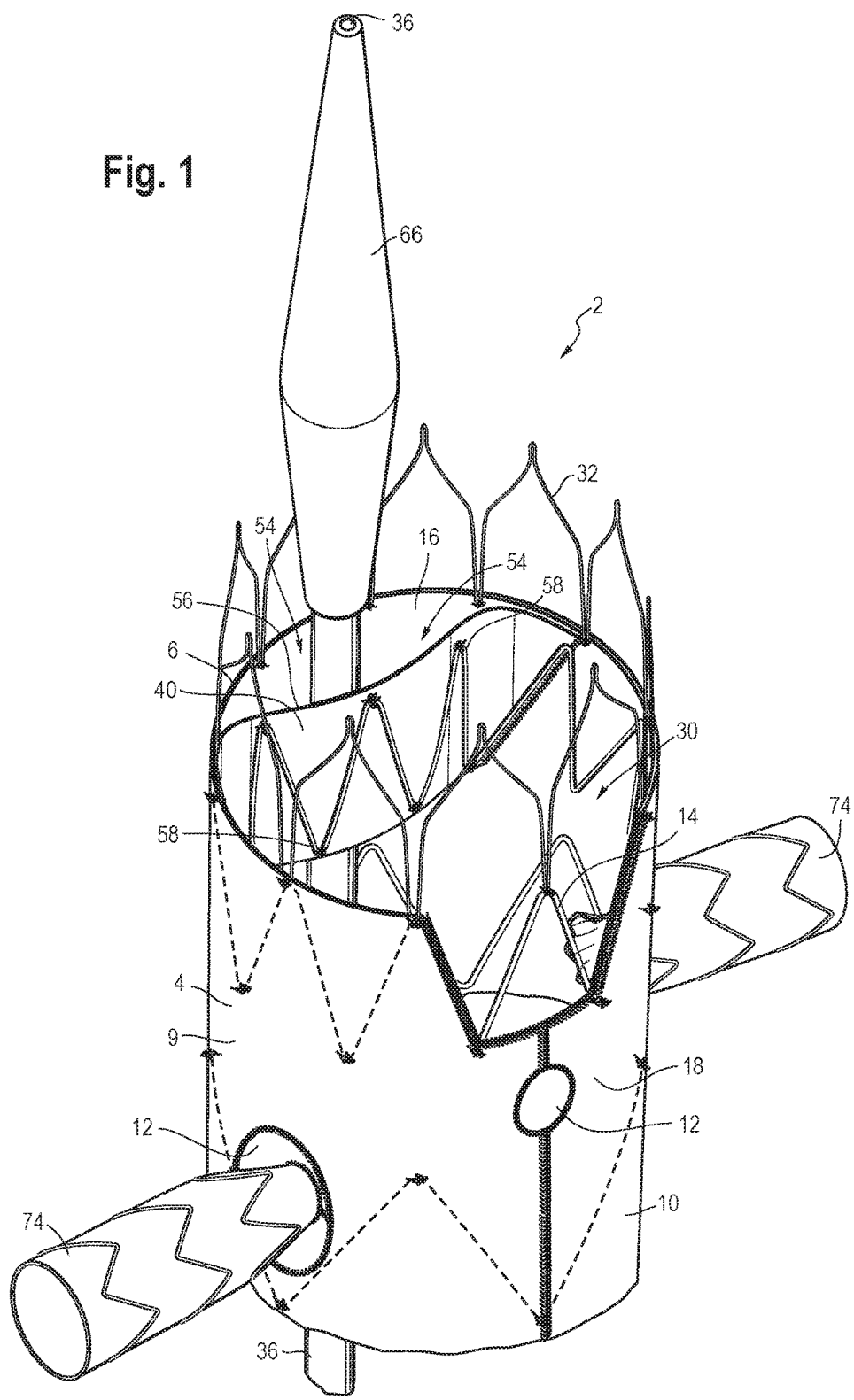
FIG. 1 is a partial perspective view of a stent graft assembly having a patch holding an end of an introducer device against the inner wall of the stent graft.

FIG. 1 is a partial perspective view of a stent graft assembly having a patch holding an end of an introducer device against the inner wall of the stent graft.

As shown in FIG. 1, a stent graft assembly 2 consists generally of a tubular stent graft 4 having a proximal end 6 and a distal end (not shown), a tubular body 9, and a lumen 30 extending therethrough. The tubular body 9 may have a first open end (proximal end 6) and a second open end (distal end). Fluid may flow through the first open end 6 and out the second open end. The stent graft 4 may be any suitable length. In one example, the stent graft 4 is a suitable length corresponding to the length of the lesion site at which the stent graft 4 is to be positioned.

The stent graft 4 may be in a compressed or collapsed configuration (not shown) or a radially-expanded configuration. In the expanded configuration it may apply a radially outward force upon at least a portion of a vessel, duct, or lumen, e.g., to maintain patency within a passageway.

The stent graft 4 may be any suitable selected diameter and may be constructed of any biocompatible graft material 10 which is suitable for facilitating repair of an injured or diseased body vessel. The graft material 10 may be synthetic and/or naturally-derived material. Synthetic biocompatible polymers may include but are not limited to polyethylene terephthalate, polyurethane, nylon, polyester, high molecular weight polyethylene, polytetrafluoroethylene, or combinations thereof. The graft material 10 can be porous or non-porous and also may be impregnated or coated with one or more therapeutic substances. In one example, the graft material 10 may be constructed of the commercially available material referred to as Dacron. The graft material 10 should have sufficient flexibility to allow for navigation of the vasculature and delivery to a targeted area in the body. Preferably, the graft material 10 is a low profile material or an ultralow profile material.

The tubular body 9 may have a sidewall 8 comprised of graft material 10. The sidewall 8 may have one or more openings or fenestrations 12 formed therein for providing fluid access to branch vessels, such as the renal arteries. In one example, stent graft 4 may have two fenestrations 12 located near the proximal end 6 of the stent graft 4. One or more connection stents 74 may be deployed in one or more fenestrations 12.

One or more stents 14 may be located on an interior surface 16, exterior surface 18, or both of the tubular body 9 of the stent graft 4. The stents 14 may be in a ring configuration. Alternatively, the stent graft 4 may be unsupported along its length such that there are no body stents located on the graft material 10 between the proximal end 6 and distal end (not shown) of the stent graft 4.

In one example, stent 14 may be a Z-stent. For example, stent 14 may have a distal end 20 with a series of distal apices 22 and a proximal end 24 with a series of proximal apices 26. Stent 14 may also have one or more elongate struts 28 connecting the distal apices 22 to the proximal apices 26.

Suitable stents 14 for use in connection with the stent graft 4 described herein may be self-expanding or mechanically-expandable stents or both, and may be deployed according to conventional methodology. A self-expanding stent may be manufactured from a shape-memory alloy, such as nickel titanium alloy (Nitinol). If the stent comprises a self-expanding material such as Nitinol, the stent may be heat-set into the desired expanded state whereby the stent can assume a relaxed radially expanded configuration. The stent may be made from other metals and alloys that allow the stent to return to its original expanded configuration upon deployment, such as, for example, stainless steel, cobalt-chrome alloys, amorphous metals, and/or non-metallic materials as would be recognized by one of skill in the art. Additionally or alternatively, the stent graft 4 may be mechanically expanded, such as through the use of an expandable balloon placed within a lumen 30 of the stent graft 4 and then radially outwardly expanded to thereby expand the stent graft 4.

The stent graft 4 may be anchored to an interior wall of a body vessel, duct, or lumen proximally and/or distally to a lesion site. For example, a proximal end 6 of the stent graft 4 may be anchored to a main vessel wall proximal to an aneurysm. The proximal end 6 of the stent graft 4 may include an anchor 32. Suitable anchors 32 include any means for attaching stent graft 4 to a body vessel wall (not shown). In one example, an anchor 32 may be attached or adhered to the proximal end 6 of the stent graft 4 by any means, including but not limited to welding, stitching, bonding, and adhesives. In one example, the anchor 32 comprises a bare fixation stent attached to the proximal end 6 of the stent graft 4. The anchor 32 may include barbs (not shown) to assist with fixation to an inner surface of the vessel, duct, or lumen in which the graft the placed.

A cannula 36 may be disposed in the lumen 30 of stent graft 4. The cannula 36 may have a proximal end 38 and a distal end (not shown). The cannula 36 includes, but is not limited to, any tube or wire that can be disposed through the lumen 30 of the stent graft 4, including guide wires and catheters. The cannula 36 may be partially disposed between a constraining patch 40 and the inner surface 16 of the tubular body 9 of the stent graft 4. The constraining patch 40 may provide an additional passageway 54 through the lumen 30 of the stent graft 4.

FIG. 2 shows a flattened view of the upper end of the internal surface of the stent graft assembly shown in FIG. 1. FIG. 3 shows a latitudinal cross-sectional view of the stent graft assembly shown in FIG. 2 at line A.

The constraining patch 40 may extend partially or entirely circumferentially around the interior surface 16 of the tubular body 9 of the stent graft 4. In one example (shown in FIGS. 1-3, and in particular FIG. 2), the constraining patch 40 extends only partially circumferentially around the interior surface 16 of the tubular body 9 of the stent graft 4.

The constraining patch 40 may be located longitudinally along the length of the stent graft 4. In one example, the constraining patch 40 is disposed at the same longitudinal or circumferential plane or proximal to one or more fenestrations 12 on the stent graft 4. In one example, the constraining patch 40 may be circumferentially offset from a fenestration 12. In one example, the constraining patch 40 may be attached to the interior surface 16 near the first open end of the tubular body 9 (the fluid inlet end 6).

The constraining patch 40 may be disposed anywhere on the circumference of the stent graft 4. In one example, the constraining patch 40 is disposed on the interior surface 16 substantially or completely opposite one or more fenestrations 12. In one example, one or more fenestrations 12 are disposed on the anterior side 60 of the interior surface 16 of the stent graft and the constraining patch 40 is on the posterior side 62 of the interior surface 16 of the stent graft 4. In another example, the constraining patch 40 extends circumferentially on the anterior side 60 of the interior surface 16 and a fenestration 12 is on the posterior side 62 of the tubular body. In one example the patch is located in a position furthest from the fenestration 12 to avoid contact with the fenestration 12 or any secondary devices that may be located in a fenestration 12. In one example, the constraining patch 40 is located on the posterior side of the graft.

The constraining patch 40 may be any suitable shape and size. For example, the constraining patch 40 may be square, rhomboidal, trapezoidal, rectangular, or irregular in shape. As shown in FIG. 2, the constraining patch 40 may have an isosceles trapezoid shape with sides 44, 46, 48, and 50. In particular, sides 46 and 50 may be parallel to each other, with side 46 distal to side 50. Sides 44 and 48 may be spaced circumferentially from each other. In one example, the constraining patch may be approximately 30-50 mm long and 15-25 mm wide.

As shown in FIGS. 1-3, the constraining patch 40 may be attached to the interior surface 16 of the tubular body 9 of the stent graft 4. The constraining patch 40 may be attached to the stent graft 4 by any suitable means, including but not limited to welding, bonding, stitching, and adhesives. In one example, the constraining patch 40 may be releasably attached to the stent graft 4.

The constraining patch 40 may be attached at one or more sides 44, 46, 48, and 50. In one example, the constraining patch 40 may have at least one attached section and at least one unattached section. For example, as shown in FIGS. 1-3, the constraining patch 40 may be attached to the interior surface 16 of the tubular body 9 near sides 44 and 48. In particular, the stitch line 52 shows where the constraining patch 40 is attached to the graft material 10 of the stent graft 4. In one example, the stitch line 52 is parallel to one of the elongate struts 28 on stent 14. Sides 46 and 50 of the constraining patch 40 may be unattached to the stent graft 4. In other words, the sides of the constraining patch 40 are attached to the stent graft 4, but the top and bottom of the constraining patch 40 are not attached to the stent graft 4. Therefore, the constraining patch 40 may have a first open end towards the first open end of the stent graft and a second open end towards the stent graft second open end. In one example, a passageway 54 is created between the constraining patch 40 and the interior surface 16 of the stent graft 4. In one example, the open ends of a constraining patch 40 may not be exposed to the exterior of the stent graft 4.

In one example shown in FIGS. 1-3, the one or more stents 14 may be attached to an interior surface 56 of the constraining patch 40, such that the constraining patch 40 can be disposed between the stent 14 and the tubular body 9. The one or more stents 14 may be attached at one or more attachment points 58. In one example, attachment points 58 may occur at or near a proximal apiece 26 or a distal apiece 22.

The constraining patch 40 can be made from any suitable patch material 42, including any biocompatible graft material. The graft material 10 may be synthetic and/or naturally-derived material. Synthetic biocompatible polymers may include but are not limited to polyethylene terephthalate, polyurethane, nylon, polyester, high molecular weight polyethylene, polytetrafluoroethylene, or combinations thereof. The graft material 10 can be porous or non-porous and also may be impregnated or coated with one or more therapeutic substances. In one example, the graft material 10 may be constructed of the commercially available material referred to as Dacron. The graft material 10 may have openings or fenestrations 12 formed therein for providing fluid access to branch vessels, such as the renal arteries. The graft material 10 should have sufficient flexibility to allow for navigation of the vasculature and delivery to a targeted area in the body. Preferably, the graft material 10 is a low profile material or an ultralow profile material.

The passageway 54 created between the constraining patch 40 and the interior surface 16 of the stent graft 4 may be in a closed position such that the constraining patch 40 abuts or lies flat against the interior surface 16 of the stent graft 4. In one example, the passageway 54 may be biased towards the closed position because a resilient stent attached to the constraining patch 40 may radially urge the constraining patch 40 into the interior surface 16 of the stent graft. The passageway 54 may also be in an open configuration (see FIGS. 1 and 3) such that a cannula 36, guide wire (not shown), dilator 66, or other introducer may pass through the passageway 54.

As shown in FIG. 3, the stent graft 4 has a main lumen 64. The passageway 54 is created when the constraining patch 40 is in an open configuration. The constraining patch 40 circumferentially separates the main lumen 64 from the constraining lumen or passageway 54. However, the main lumen 64 and the passageway 54 remain in fluid communication due to the unattached sides of the constraining patch 40.

As shown in FIGS. 1 and 3, a cannula 36 can be preloaded in the passageway 54. The cannula 36 may be configured to receive one or more guide wires 66 or catheters. The constraining patch 40 is configured to temporarily constrain a portion of a medical instrument within the passageway 54. In one example, the constraining patch 40 may hold the cannula 36 snugly against the interior surface 16 of the stent graft 4. The constraining patch 40 may constrain a cannula 36 disposed in the passageway 54 because it can constrain the cannula 36 from latitudinal movement outside the passageway 54. In addition, even a portion of cannula 36 that is not disposed in the passageway 54 by constraining patch 40 may be biased by the constraining patch 40 such that it is partially restricted from latitudinal movement.

Figure 4:
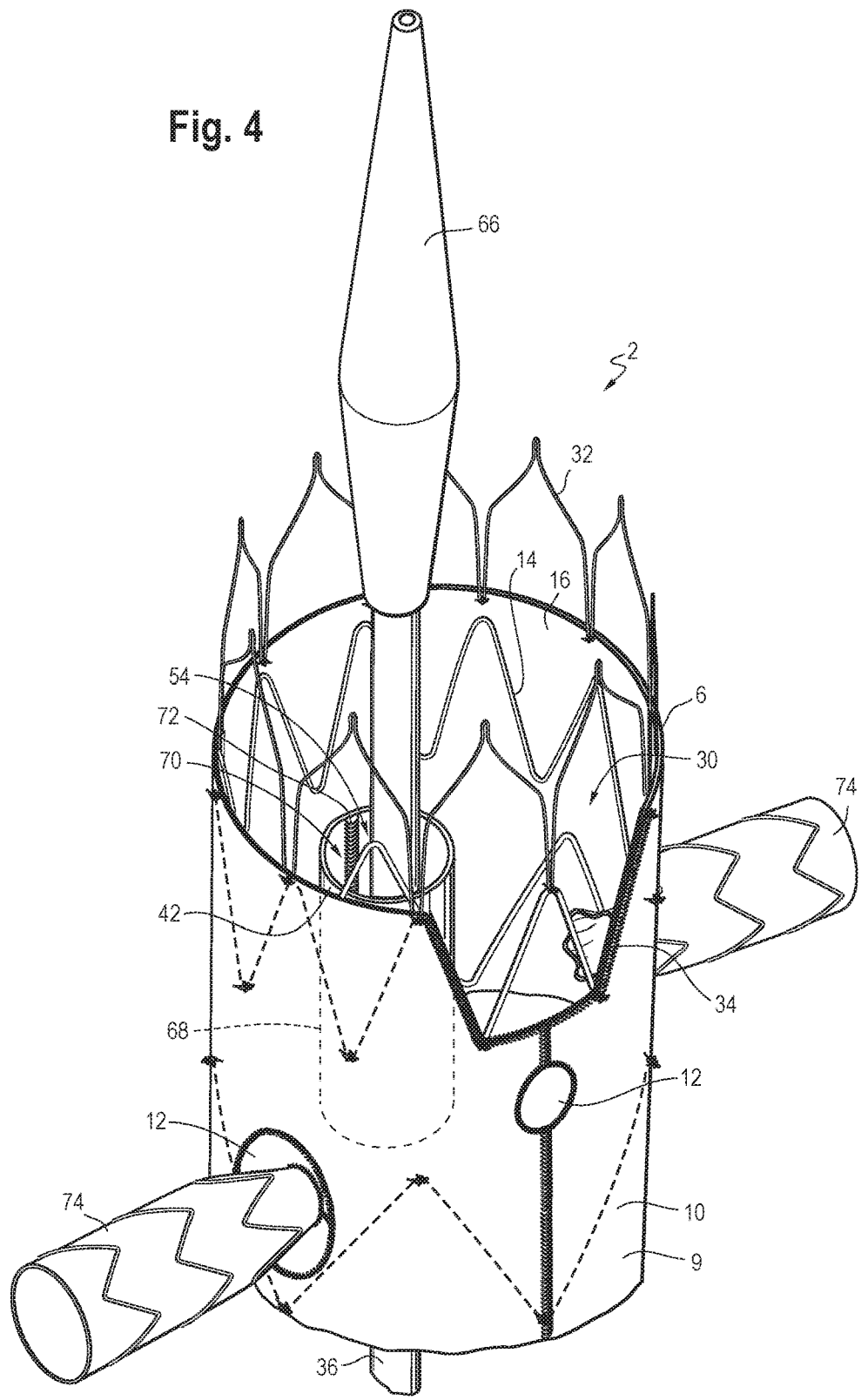
FIG. 4 shows an alternative embodiment of stent graft assembly where the tubular body has a scallop.
Figure 5:
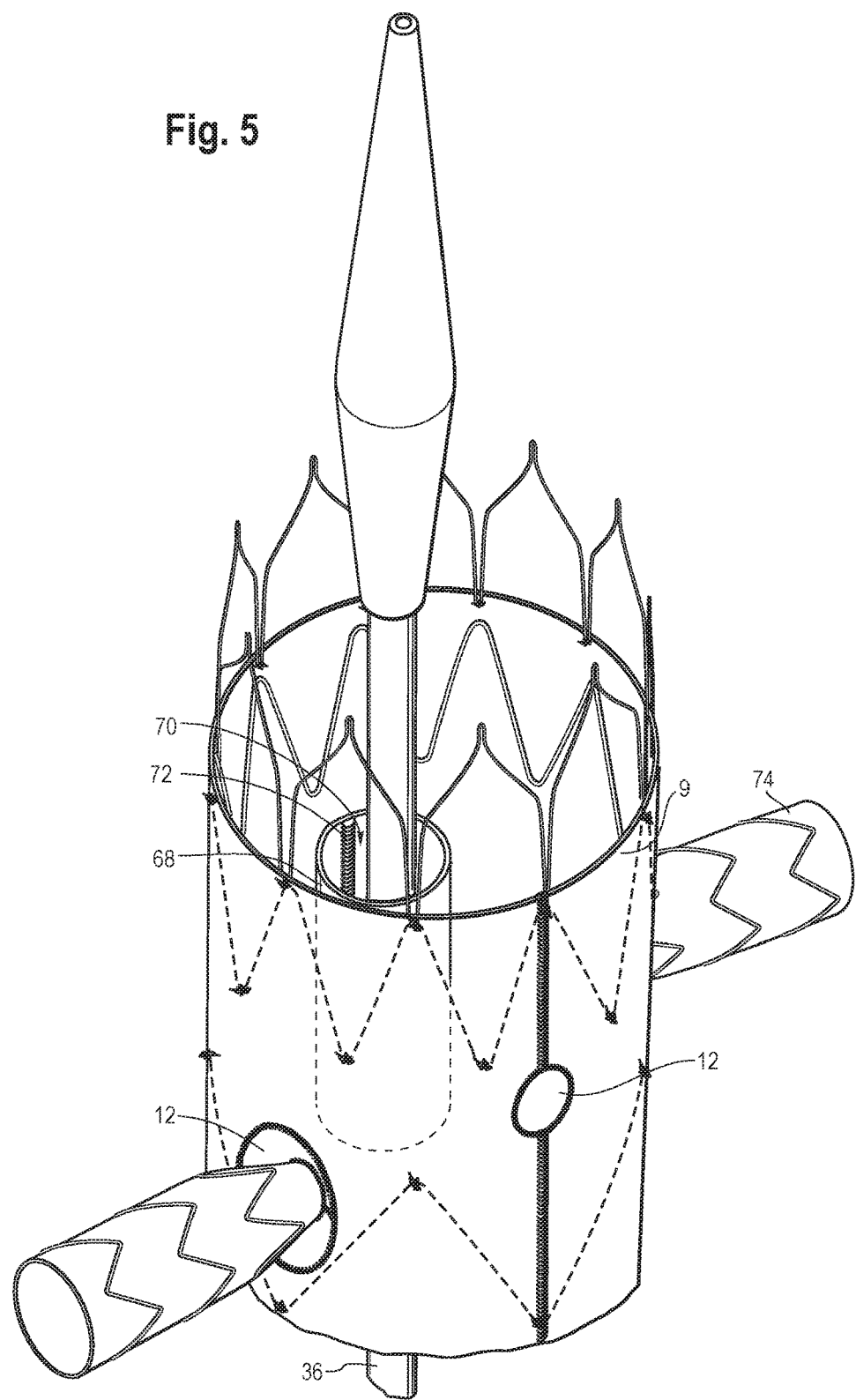
FIG. 5 shows an alternative embodiment of stent graft assembly where the tubular body does not have a scallop.

FIGS. 4-7 shows an alternative embodiment of a stent graft assembly. FIG. 4 shows an alternative embodiment of stent graft assembly where the tubular body 9 has a scallop 34. FIG. 5 shows an alternative embodiment of stent graft assembly where the tubular body 9 does not have a scallop. Instead, as shown in FIG. 5, the proximal end of the tubular body 9 continues circumferentially around the most proximal stent.

FIG. 6 shows a flattened view of the upper end of the internal surface of the stent graft assembly shown in FIG. 4. FIG. 7 shows a latitudinal cross-sectional view of the stent graft assembly shown in FIG. 6 at line B.

The alternative embodiment shown in FIGS. 4-7 is generally similar to the embodiment illustrated in FIGS. 1-3. However, in the embodiment shown in FIGS. 4-7 the constraining patch 40 may form a tube 68 with a tubular constraining lumen 70.

The constraining patch 40 may be any suitable shape, including rectangular-shape as shown in FIGS. 5-7. In one example, the constraining patch may be approximately 15-25 mm long and 4-10 mm in diameter.

The constraining patch 40 may be attached to the stent graft 4 at attachment point 72. As shown in FIG. 4, the constraining patch 40 may be sewn to the interior surface 16 of the stent graft 4 at stitch line 52. In one example, sides 44 and 48 of the constraining patch 40 are attached at stitch line 52 and sides 46 and 50 of the constraining patch 40 may be unattached to the stent graft 4. In other words, the sides of the constraining patch 40 are attached to the stent graft 4, but the top and bottom of the constraining patch 40 are not attached to the stent graft 4. In one example, the open ends of a constraining patch 40 may not be exposed to the exterior of the stent graft 4.

In one example, a tubular constraining lumen 70 is created when the constraining patch 40 is sewn into the stent graft 4. In this way, the tubular constraining lumen 70 may be in fluid communication with the main lumen 30 in the stent graft 4.

The constraining patch 40 may be attached to the stent graft 4 using any suitable method including but not limited to welding, bonding, stitching, and adhesives. In one example, the constraining patch 40 is attached to the stent graft 4.

The constraining patch 40 can have a weak section or frangible portion extending longitudinally along its length that is susceptible to breaking. The weak section may be broken with a balloon or any other method so that the constraining patch 40 may lay flat against the wall of the graft 4. In one example, the weakened stitch line (not shown) is across from the stitch line 52 that attaches the constraining patch 40 to the graft 4.

The tubular constraining lumen 70 may be configured to temporarily hold a medical device 36, such as the introducer for the stent graft, away from the fenestration. In other examples, the patch may hold another device. In one example, the constraining lumen 70 preferably has a diameter of 8-10 mm.

As mentioned previously, the constraining patch 40 may be configured to hold a medical device 36. If the cannula of the primary device (for example, a fenestrated or branched graft in a modular system) is preloaded going through the passageway 54 or tubular constraining lumen 70 of the constraining patch 40, when the primary device is deployed the guide wire 66 can remain constrained by constraining patch 40. As a result, any secondary devices (not shown) that run over this guide wire 66 can be constrained against the interior surface 16 of the stent graft 4.

Figure 8:
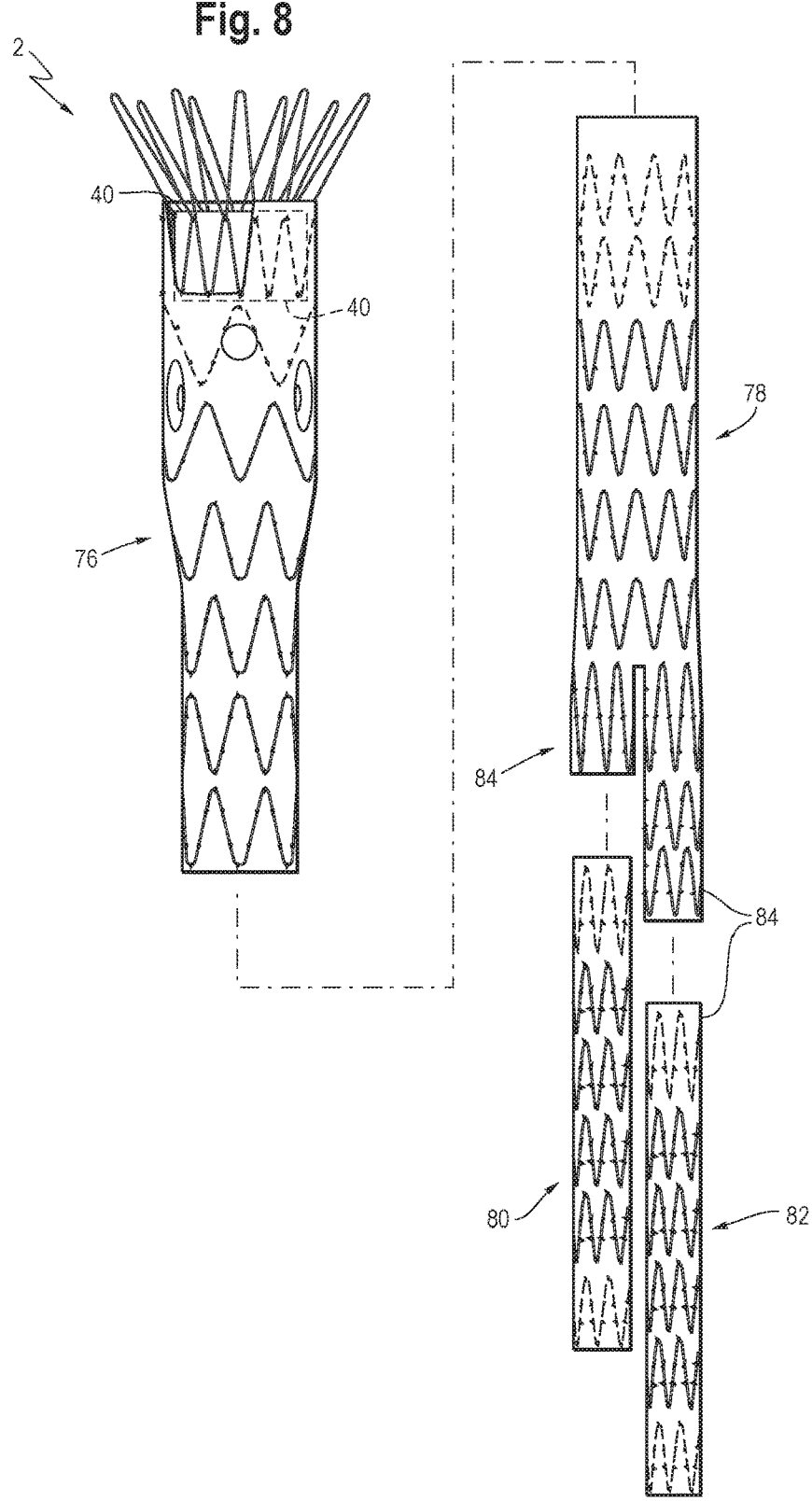
FIG. 8 is an exploded view of a stent graft assembly having a patch configured to hold an introducer device against the inner wall of the stent graft.

FIG. 8 is an exploded view of a stent graft assembly having a patch configured to hold an introducer device against the inner wall of the stent graft.

As shown in FIG. 8, one or more tubular stent-grafts may be combined to form a stent graft assembly 2. In this example, the assembly 2 includes a first stent graft component 76, a second stent graft component 78, a third stent graft component 80, and a fourth stent graft component 82. The proximal end of stent graft component 78 may be implanted in the distal portion of the first stent graft component 76. The proximal end of stent graft components 80 and 82 may be implanted in mating regions 84 on the stent graft component 78.

The first stent graft component 76 may include a constraining patch 40 such as the one shown and described in FIGS. 1-7 above.

Referring generally to FIG. 1-8, when one or more connection stents 74 are deployed in one or more fenestrations 12, it can be particularly advantageous to position the constraining patch 40 and constrain the cannula 36 further from the connection stents 74 in such a way that a cannula 36 is less likely to have unwanted incidental contact with other connection stents that may be disposed in the main lumen 64 of the stent graft 4. Similarly, when one or more bridging stents are deployed in a stent graft 4, it may be advantageous to constrain a cannula 36 further from a bridging stent so as to avoid incidental contact.

The disclosed constraining patch 40 can constrain a section of the cannula 36 so that the rest of the cannula 36 can follow a more predictable path at the point of constrainment and also through the rest of the main lumen 64.

This restriction of movement helps prevent unwanted contact with other features of the stent graft (such as connection stents 74). For example, a constrained cannula 36 is less likely to have unintentionally contact with a connection stent 74, and therefore less likely to cause undesired movement or damage (e.g. denting or compression) to the connection stent. Undesired movement or damage of a connection stent may increase the complication and patient risk. As a result, the constraining patch 40 can help constrain and control a cannula 36 traveling through the interior of the stent graft 4 from unwanted movement.

The clinical advantages of restricting unwanted cannula movement include: reducing adverse events associated with visceral vessel and reducing secondary intervention to correct problems caused by damaged connection stent. For example, using the constraining patch can 1) reduce need for additional precautionary steps to avoid damaging connection stents; 2) reduce need for re-ballooning stents; 3) reduce need for future secondary intervention; and 4) save resources such as time and money. As such, using the constraining patch can result in less complications during the procedure and less risk of patient injury.

In one example, the constraining patch can prevent problems from occurring with medical produces while at the same time not requiring any additional steps or changes in procedure for the operating physician.

The embodiments and figures above are merely exemplary and should not be construed as limiting the claims. It is also contemplated that minor variations may without varying from the inventive concept covered by the claims below.

While various embodiments of the invention have been described, the invention is not to be restricted except in light of the attached claims and their equivalents.

We claim:

1. A stent graft assembly comprising:
   A delivery catheter;
   a tubular body disposed over the delivery catheter and having a first open end, a second open end, a main lumen between the first open end and the second open end, and an inner surface surrounding the main lumen;
   a patch disposed in the main lumen and attached to the inner surface and defining a longitudinally extending passageway between the inner surface and the patch, the patch having a first unattached end and a second unattached end, wherein the delivery catheter extends through the longitudinally extending passageway between the inner surface and the patch and is preloaded within the longitudinally extending passageway;
   wherein the passageway is in fluid communication with the main lumen through the first unattached end and the second unattached end;
   wherein neither unattached end is in communication with an exterior of the graft; and
   wherein in a first configuration the longitudinally extending passageway of the patch is open and configured to temporarily constrain a portion of the delivery catheter within the passageway and in a second configuration is closed and lies flat against a wall of the tubular body.

2. The stent graft assembly of claim 1 wherein the tubular body comprises graft material having a sidewall and a fenestration in the sidewall.

3. The stent graft assembly of claim 2 wherein the patch is circumferentially offset from the fenestration.

4. The stent graft assembly of claim 2 wherein the tubular body has a posterior side and an anterior side, and wherein the patch extends at least partially around a circumference of the inner surface; and wherein the fenestration is on the posterior side and the patch is on the anterior side.

5. The stent graft assembly of claim 1 wherein the patch has at least two lateral edges and the patch is attached to the inner surface at the at least two lateral edges.

6. The stent graft assembly of claim 1 further comprising at least one stent ring.

7. The stent graft assembly of claim 6 wherein the stent is disposed at least partially over the patch and in a first configuration closes the passageway.

8. The stent graft assembly of claim 1 further comprising:
a fenestration in the tubular body,
wherein the first open end is a fluid inlet end and the patch is attached to the inner surface at the first open end.

9. The stent graft of claim 1, wherein the patch comprises a longitudinal tube of graft material having a first open end toward the stent graft first open end and a second open end toward the stent graft second open end.

10. A stent graft assembly comprising:
a tubular body having a main lumen and an inner surface surrounding the main lumen;
a patch disposed in the main lumen, an inflow end and an outflow end, the patch comprising a piece of material attached to the inner surface that forms a passageway that extends at least longitudinally along the patch and has a first open end and a second open end;
wherein the passageway has a first configuration where a portion of the patch extends away from the inner surface and the passageway is open, and a second configuration where the patch lays flat against the inner surface and the passageway is closed, and
wherein in both the first and second configurations the patch does not obstruct fluid flow through the main lumen and the outflow end.

11. The stent graft assembly according to claim 10 wherein the patch extends partially around a circumference of the inner surface.

12. The stent graft assembly according to claim 10 further comprising
a stent ring disposed about the inner surface and at least partially over the patch.

13. The stent graft assembly according to claim 12 wherein the patch has at least one lateral edge aligned with a strut of the stent ring and wherein the patch is attached to the inner surface at the at least one lateral edge.

14. The stent graft assembly of claim 13 wherein the patch has at least two lateral edges and is attached to the inner surface at the at least two lateral edges.

15. The stent graft assembly of claim 10 wherein the passageway is configured to temporarily receive a medical instrument.

16. The stent graft assembly according to claim 12 wherein the patch is located between the stent ring and the inner surface.

17. A stent graft delivery assembly comprising:
a delivery catheter;
a stent graft disposed over the delivery catheter having a main lumen and an inner surface surrounding the main lumen;
a patch disposed in the main lumen and attached to the inner surface;
the patch forming a constraining tube having a longitudinal constraining lumen extending therethrough, wherein the constraining tube has first and second open ends and wherein neither open end is exposed to an exterior of the stent graft,
wherein the delivery catheter extends through the constraining tube and is preloaded within the constraining tube when the stent graft is deployed, and
wherein in a first configuration the lumen of constraining tube is open and configured to temporarily constrain a portion of the delivery catheter within the constraining tube and in a second configuration lies flat against the inner surface.

18. The stent graft assembly according to claim 17 wherein the constraining tube has a frangible portion extending longitudinally therealong that is susceptible to breaking.

19. The stent graft assembly of claim 17, wherein the stent graft has a posterior side and an anterior side, where the constraining tube is on the anterior surface of the stent graft and further comprising a fenestration on the posterior surface of the stent graft.

20. A stent graft assembly comprising:
a delivery catheter for delivering the stent graft to the body lumen;
a stent graft disposed over the delivery catheter having a main lumen and an inner surface surrounding the main lumen, the stent graft having a plurality of fenestrations in a side wall of the stent graft;
a patch disposed entirely within the main lumen and attached to the inner surface at a location offset from each of the plurality of fenestrations;
the patch having a longitudinal constraining lumen extending therethrough,
wherein the delivery catheter extends through the longitudinal constraining lumen and is preloaded within the constraining tube when the stent graft is deployed, and
wherein the patch temporarily constrains the delivery catheter against the inner surface and away from the plurality of fenestrations and at least partially restricts latitudinal movement of the delivery catheter within the main lumen.

* * * * *